United States Patent
Nagasaki et al.

(10) Patent No.: US 9,849,186 B2
(45) Date of Patent: Dec. 26, 2017

(54) TRIBLOCK COPOLYMER AND USE THEREFOR

(71) Applicant: UNIVERSITY OF TSUKUBA, Ibaraki (JP)

(72) Inventors: Yukio Nagasaki, Ibaraki (JP); Min Ley Pua, Ibaraki (JP); Pennapa Chonpathompikunlert, Ibaraki (JP); Toru Yoshitomi, Ibaraki (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 0 days.

(21) Appl. No.: 14/374,015

(22) PCT Filed: Jan. 24, 2013

(86) PCT No.: PCT/JP2013/051395
§ 371 (c)(1),
(2) Date: Jul. 23, 2014

(87) PCT Pub. No.: WO2013/111801
PCT Pub. Date: Aug. 1, 2013

(65) Prior Publication Data
US 2014/0356315 A1  Dec. 4, 2014

(30) Foreign Application Priority Data

Jan. 24, 2012 (JP) .................................. 2012-012279

(51) Int. Cl.
| | | |
|---|---|---|
| A61K 31/00 | (2006.01) | |
| A61K 47/00 | (2006.01) | |
| A61K 9/00 | (2006.01) | |
| A61K 47/48 | (2006.01) | |
| C08F 8/32 | (2006.01) | |
| C08F 293/00 | (2006.01) | |
| A61K 31/445 | (2006.01) | |
| C08F 12/18 | (2006.01) | |

(52) U.S. Cl.
CPC ...... *A61K 47/48176* (2013.01); *A61K 31/445* (2013.01); *C08F 8/32* (2013.01); *C08F 12/18* (2013.01); *C08F 293/00* (2013.01); *C08F 293/005* (2013.01); *A61K 9/0019* (2013.01); *A61K 2201/21* (2013.01); *A61K 2201/326* (2013.01); *C08F 2438/02* (2013.01); *C08F 2810/40* (2013.01)

(58) Field of Classification Search
CPC .... C08F 12/18; C08F 293/00; A61K 2201/21; A61K 31/00; A61K 47/00; A61K 9/00
See application file for complete search history.

(56) References Cited

U.S. PATENT DOCUMENTS

| 7,018,655 | B2* | 3/2006 | Lele | ..................... C08F 293/00 424/450 |
|---|---|---|---|---|
| 8,980,241 | B2* | 3/2015 | Nagasaki | .................. A23L 1/30 424/78.17 |
| 2002/0192286 | A1* | 12/2002 | Shih | ....................... A61K 47/34 424/486 |
| 2003/0181613 | A1* | 9/2003 | Lele | ....................... C08F 293/00 526/222 |
| 2004/0185101 | A1* | 9/2004 | Shih | ....................... A61K 47/34 424/486 |
| 2005/0112172 | A1 | 5/2005 | Pacetti | |
| 2006/0235084 | A1* | 10/2006 | Heller | .............. A61K 47/48215 514/785 |
| 2010/0222407 | A1* | 9/2010 | Segura | ................. A61L 31/048 514/44 A |
| 2011/0142787 | A1 | 6/2011 | Nagasaki et al. | |

FOREIGN PATENT DOCUMENTS

| JP | 2007-520260 | 7/2007 |
|---|---|---|
| JP | 2010-28199 | 2/2010 |
| JP | 2010-211826 | 9/2010 |
| JP | 2010-260471 | 11/2010 |
| JP | 2011-78706 | 4/2011 |
| JP | 2011-184429 | 9/2011 |
| JP | 2012-67025 | 4/2012 |
| JP | 2012-111700 | 6/2012 |
| WO | 2009/133647 | 11/2009 |

OTHER PUBLICATIONS

Adeli et al. Preparation of Diblock and Triblock Copolymers of Styrene, 2,5-Norbornadiene, Ethylmethacrylate and PEG by Nitroxide-controlled Free Radical Polymerization. Iranian Polym. J, 2001, 6:393-402.*
Zhuang et al. Synthesis of Amphiphilic Block Copolymers Bearing Stable Nitroxyl Radicals. J. Polym. Sci.:Part A: Polymer Chemistry, 2010, 48:5404-5410.*
Nagasaki. Nitroxide radicals and nanoparticles: a partnership for nanomedicine radical deliver. Therapeutic Delivery (2012) 3(2):1:15 (and references therein).*
Lemmers et al., Transient network topology of interconnected polyelectrolyte complex micelles. Soft Matter, 2011, 7, 1378-1389.*

(Continued)

*Primary Examiner* — Robert A Wax
*Assistant Examiner* — Olga V Tcherkasskaya
(74) *Attorney, Agent, or Firm* — Wenderoth, Lind & Ponack, L.L.P.

(57) ABSTRACT

Provided is a triblock copolymer represented by General Formula (I):

$$\text{CNR-PEG-CNR} \quad (1)$$

or a polycation thereof, wherein
each CNR is independently a polymer segment having a repeating unit containing as part of a pendant group a cyclic nitroxide radical that binds to the polymer main chain via a linking group having at least one imino group or ether bond, and PEG is a segment containing poly(ethylene glycol).

9 Claims, 7 Drawing Sheets

(56) References Cited

OTHER PUBLICATIONS van der Gucht et al. Polyelectrolyte complexes: Bulk phases and colloidal systems. Journal of Colloid and Interface Science 361 (2011) 407-422.*

International Search Report dated Mar. 26, 2013 in International (PCT) Application No. PCT/JP2013/051395.

* cited by examiner

[Fig. 1]
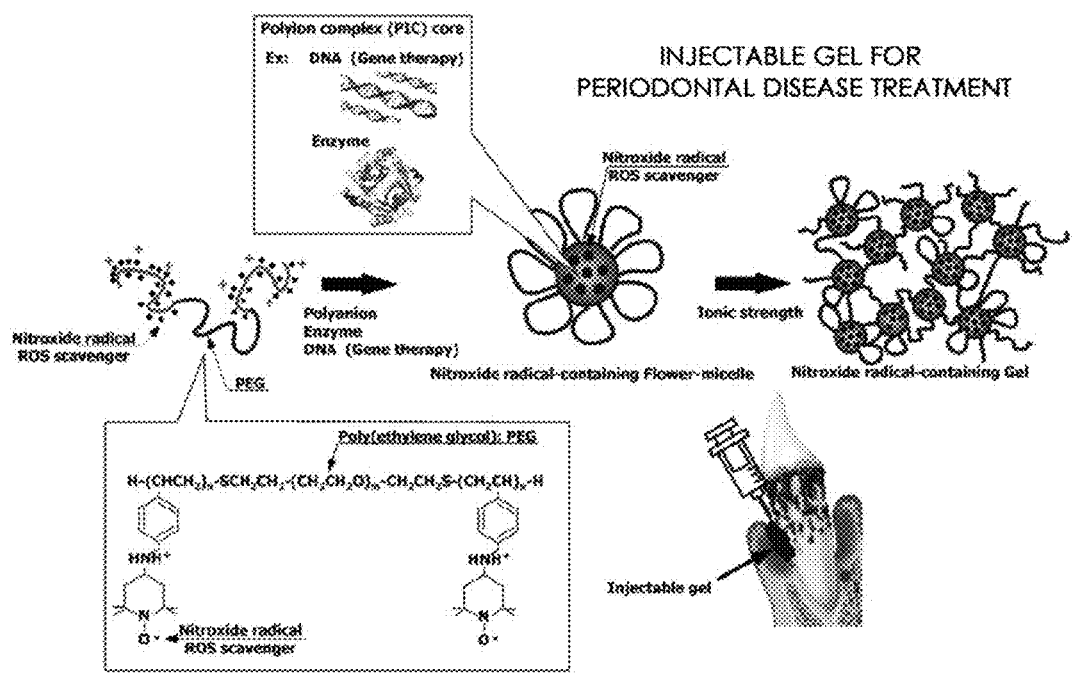
[Fig. 2]
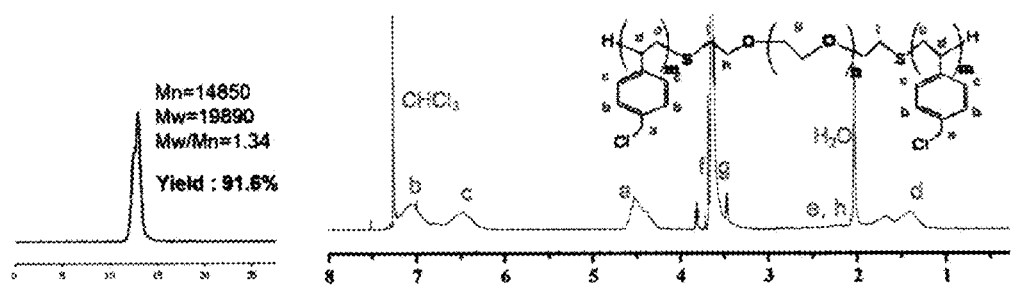
SEC AND NMR SPECTRUM OF PCMS-b-PEG-b-PCMS TRIBLOCK COPOLYMER

[Fig. 3]
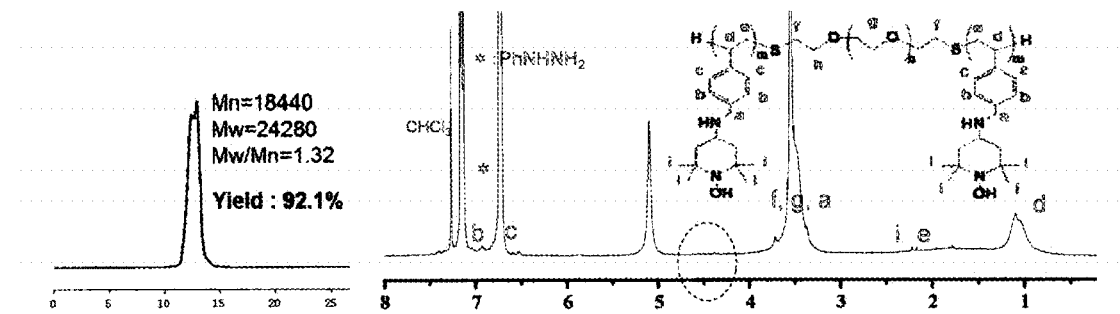
[Fig. 4]
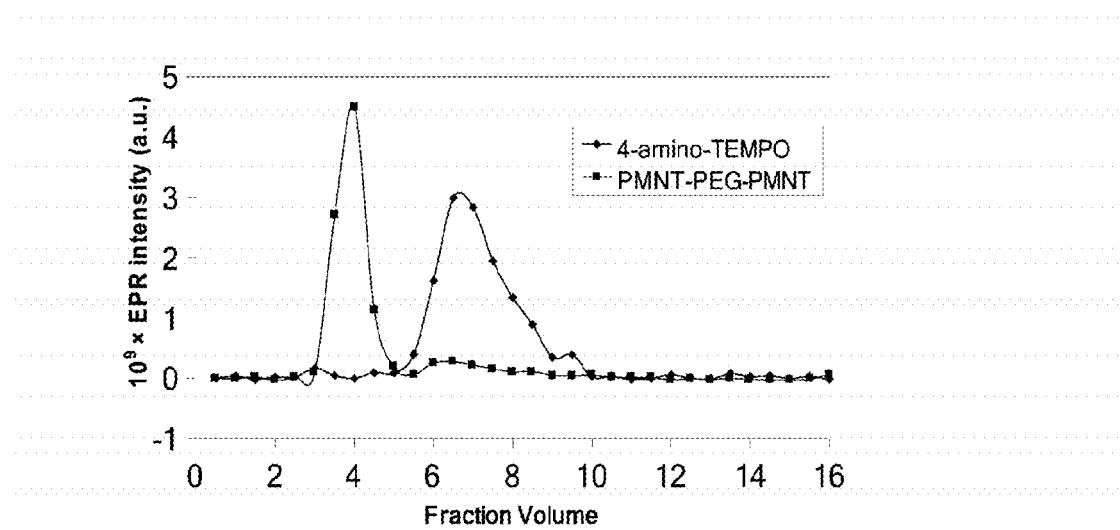

[Fig. 5]
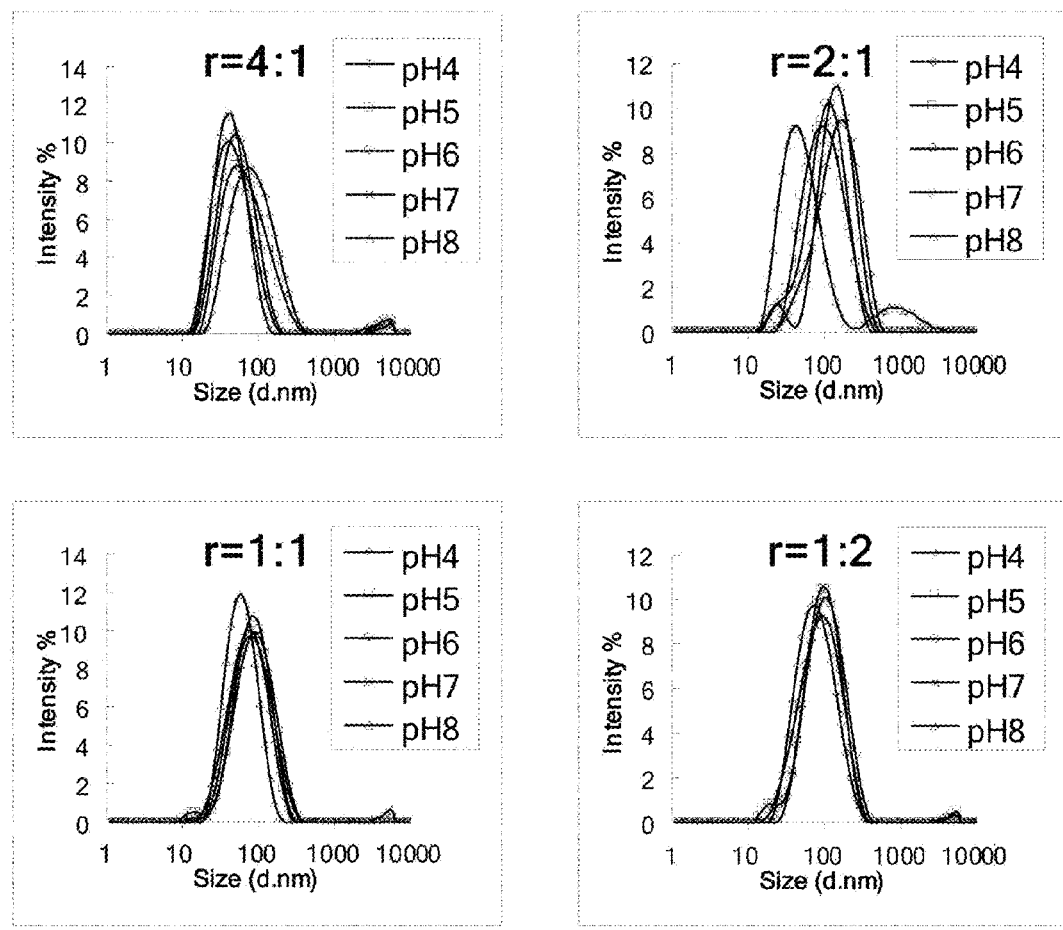
[Fig. 6]
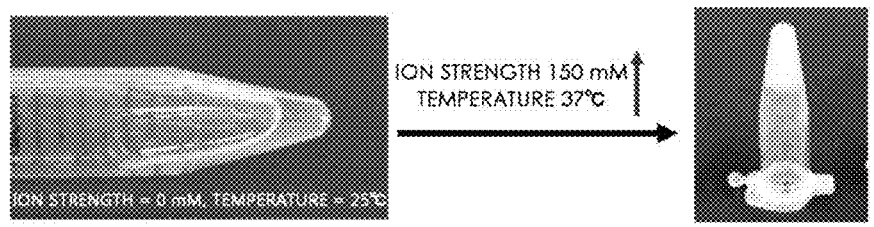

[Fig. 7]
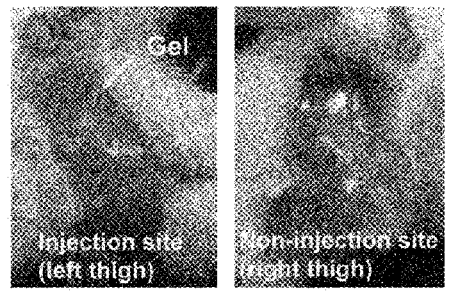
[Fig. 8]
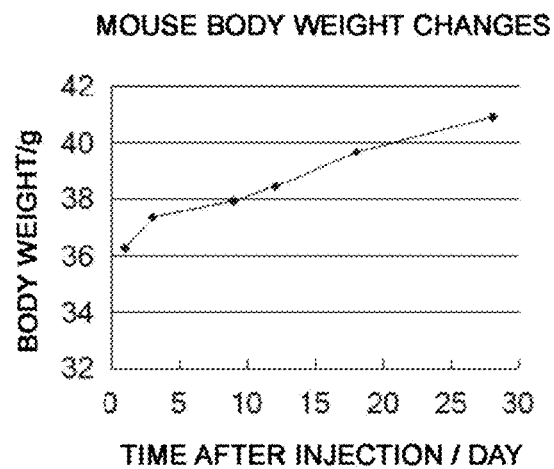
EVALUATION RESULTS FOR IN VIVO TOXICITY
OF POLYION COMPLEX GEL

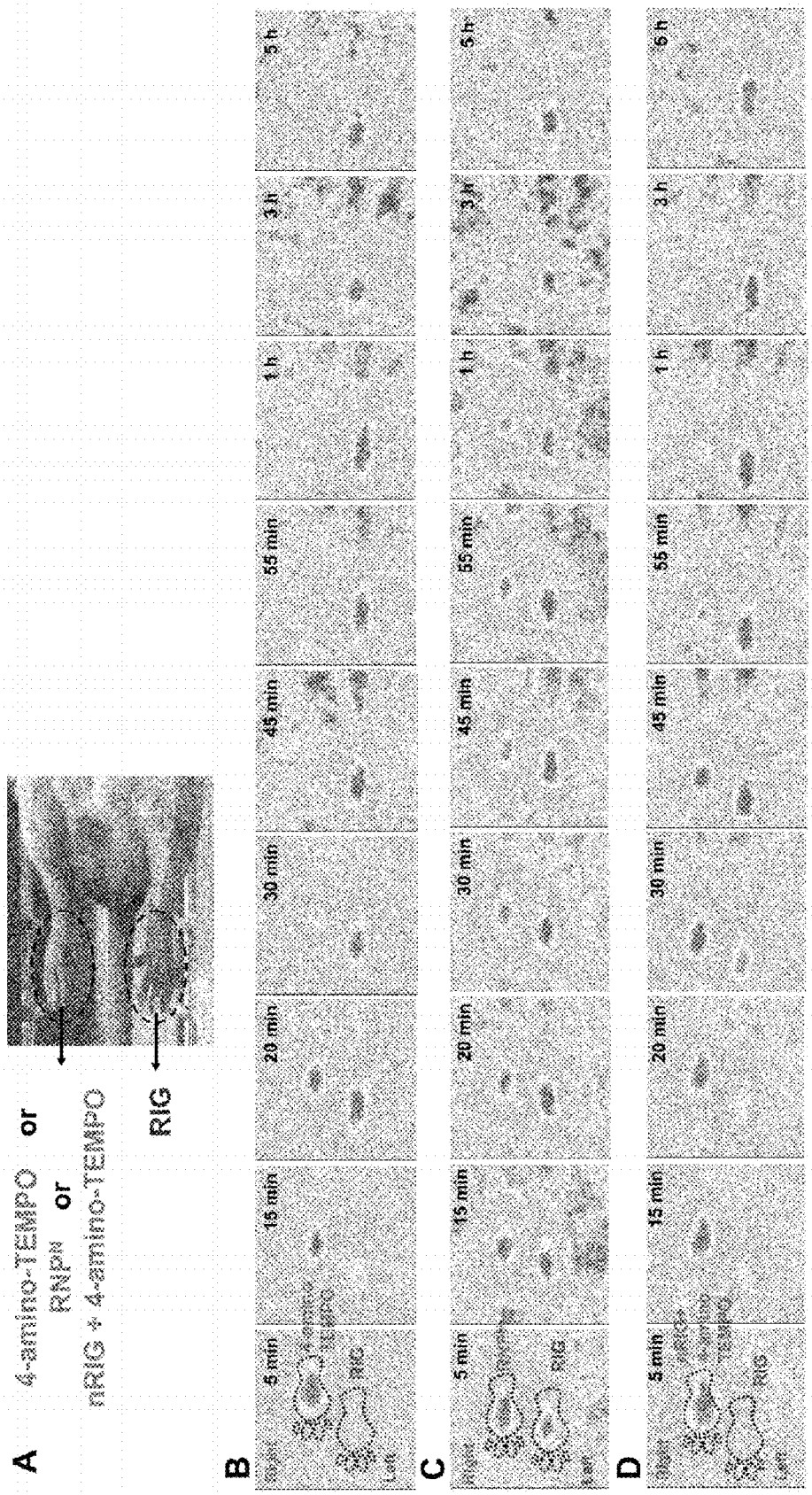

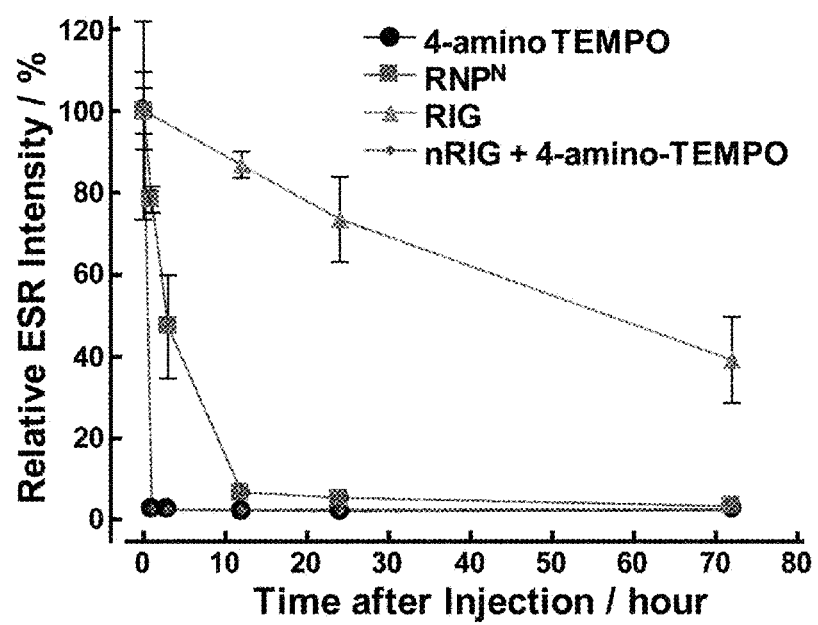
[Fig. 10]

[Fig. 11]
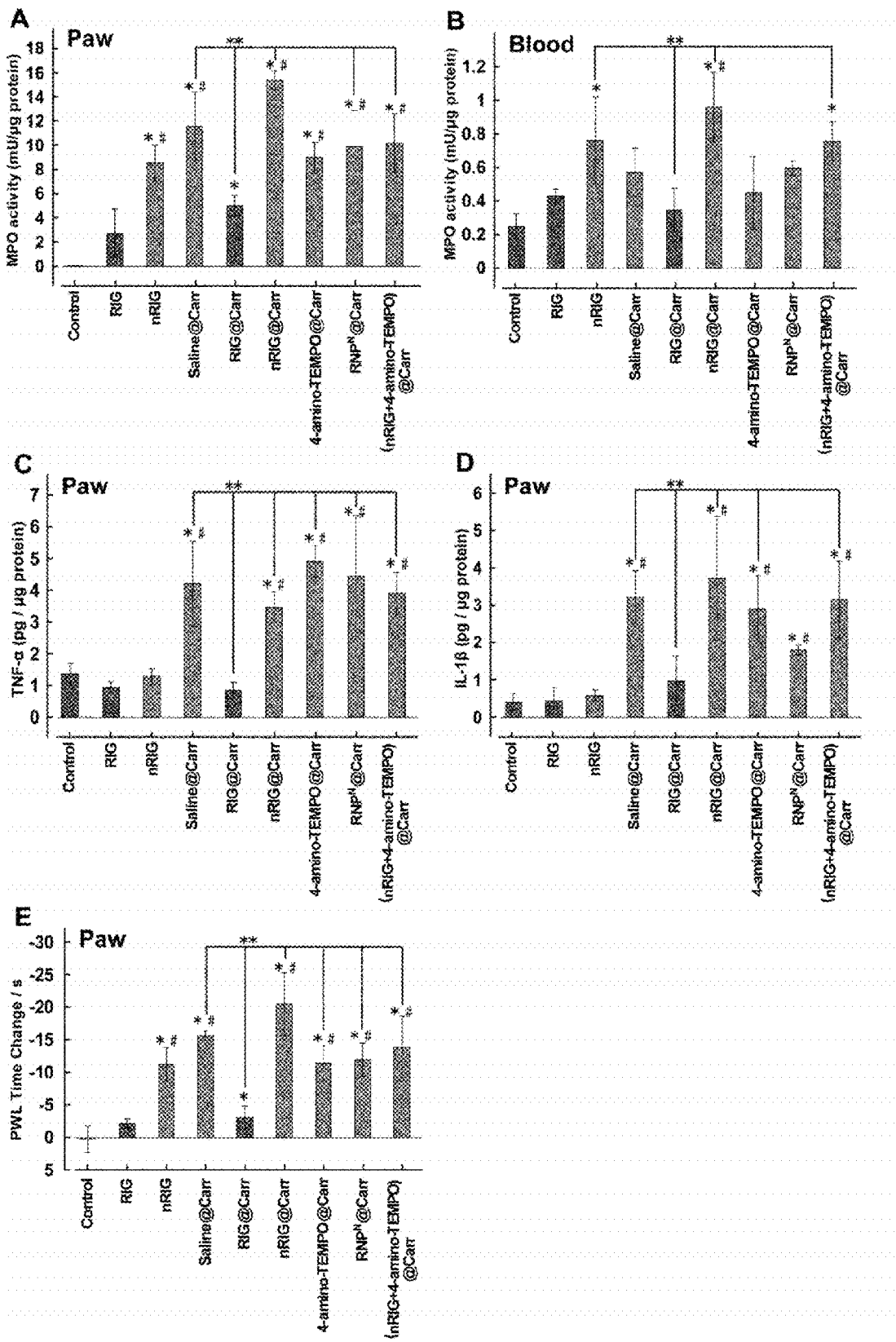

TRIBLOCK COPOLYMER AND USE THEREFOR

TECHNICAL FIELD

The present invention relates to a triblock copolymer, and relates specifically to a triblock copolymer containing two polymer blocks having cyclic nitroxide radicals as pendant groups, to with a poly(ethylene glycol) block covalently bonded to these at both ends, and relates to a composition for biological use containing this triblock copolymer as an active ingredient.

BACKGROUND ART

Reactive oxygen species (ROS) disrupt cell functioning by oxidatively denaturing lipids, proteins, sugars, nucleic acids and the like in the body. Normally the oxidation-antioxidation (redox) balance is strictly regulated in vivo, but when excess ROS are produced, the balance of oxidation-antioxidation factors tends towards oxidation. This condition is called "oxidative stress", and is known as a causative or contributing factor in various diseases. In fact, it has become clear that a variety of diseases including Alzheimer's disease, Parkinson's disease and other intractable neurological conditions, arteriosclerosis, cerebral infarction, myocardial infarction, renal failure, diabetes, cancer and the like can occur when oxidative stress increases in the body. Thus, there is demand for the development of devices capable of effectively treating oxidative stress disorders.

In particular, it has become increasingly clear in recent years that oxidative stress caused by periodontal disease plays a significant role in systemic medical conditions. In such a specific area of the body, treatment with a low-molecular-weight or polymerized ROS scavenger is an option, but these ROS scavengers have poor therapeutic effects because they are easily eliminated from specific areas of the body such as periodontal pockets. To effectively treat diseases such as periodontal disease that affect specific areas of the body, and prevent these diseases from becoming systemic, a treatment must clear three hurdles: i) it must allow injection into the specific area, such as a periodontal pocket, ii) the injected drug must be retained long-term in the periodontal pocket or other specific area, and exhibit continuing effects, and iii) the treatment must be safe and not eliminate "good active oxygen," which is involved in energy production.

In the past, the inventors have enclosed nitroxide radicals that catalytically remove active oxygen inside nanoparticles, and investigated these as intravenous or oral nanotherapies, which have been shown to be effective in cancer, ischemic disease and intestinal disease (see Patent Document 1, Patent Document 2, Patent Document 3, Patent Document 4 and Patent Document 5). In particular, nanoparticles that are designed to break down and produce an antioxidative effect at disease sites with lowered pH, such as inflammation, cancer and the like, have proved highly safe and effective. Existing nanoparticles have proved useful in the critical role of safely transporting drugs in this way.

As discussed above, however, it is also necessary to provide means by which a therapy can be retained in an area of the body and produce a continuous effect while having practically no effect on other areas of the body.

CITATION LIST

Patent Literature Document

Patent Document 1: WO 2009/133647
Patent Document 2: Japanese Patent Application Publication No. 2011-078706
Patent Document 3: Japanese Patent Application No. 2010-028199, published as Japanese Patent Application Publication No. 2011-184429
Patent Document 4: Japanese Patent Application No. 2010-211826, published as Japanese Patent Application Publication No. 2012-067025
Patent Document 5: Japanese Patent Application No. 2010-260471, published as Japanese Patent Application Publication No. 2012-111700

SUMMARY OF THE INVENTION

Technical Problem

To solve these problems, it is an object of the present invention to provide a novel material that provides enhanced safety during treatment of a living body with a polymerized drug or nanoparticles thereof, and which can be retained in a specific area of the body. As such a material, the inventors have developed a material comprising a polymerized drug or nanoparticles that are gelled in response to a specific area of the body and the surrounding environment.

The inventors have discovered that an A-B-A triblock copolymer comprising a poly(ethylene glycol) block sandwiched between two polymer blocks each containing a specific active drug residue, and particularly an active drug residue and a polycation chargeable pendant, is gelled in response to such an area of the body or surrounding environment, producing the desired activity in that area. The inventors also discovered that a triblock copolymer that has an active drug residue but also contains a non-polyion chargeable pendant group can also be used in the field.

Thus, as means for solving the above problems, the triblock copolymer represented by General Formula (I):

CNR-PEG-CNR  (I)

wherein each CNR is independently a polymer segment having a repeating unit containing as part of a pendant group a cyclic nitroxide radical that binds to the polymer main chain via a linking group having at least one imino group or ether bond, and PEG is a segment containing poly(ethylene glycol), or a salt thereof, is disclosed.

In general terms, a triblock copolymer or salt thereof is provided in which the aforementioned cyclic nitroxide radical is bound to the polymer main chain via a linking group represented by o- or p-phenylene-($C_{1-6}$ alkylene-NH)$_p$—($C_{1-6}$ alkylene)$_q$ or o- or p-phenylene-($C_{1-6}$ alkylene-O)$_p$—($C_{1-6}$ alkylene)$_q$, in which p is an integer from 1 to 3 and q is an integer from 0 to 1, and while not limited, the cyclic nitroxide radical is selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, with the unbound terminal of the phenylene binding to the polymer main chain, which is derived from polymerizable unsaturated double bonds.

The linking group is preferably o- or p-phenylene-($C_{1-6}$ alkylene-NH)$_p$—($C_{1-6}$ alkylene)$_q$. A triblock copolymer or salt thereof having such a linking group confers on the polymer the additional to function of cationic chargeability in specific acidic water.

A more specific embodiment of the present invention provides a triblock copolymer represented by General Formula (II) or a salt thereof.

[Chemical formula 1]

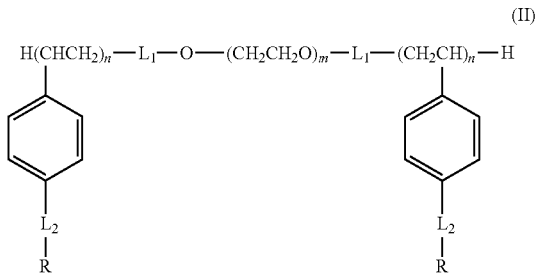

(II)

In the formula, each $L_1$ is independently selected from the group consisting of a single bond, —S—$(CH_2)_c$—, —S—$(CH)_cCO$—, —$(CH_2)_cS$— and —$CO(CH_2)_cS$—, in which c is an integer from 1 to 5; each $L_2$ is independently —$C_{1-6}$ alkylene-NH—$(C_{1-6}$ alkylene$)_q$- or —$C_{1-6}$ alkylene-O—$(C_{1-6}$ alkylene$)_q$-, in which q is 0 or 1; and at least 50% of the total number n of Rs in the formula independently represent residues of cyclic nitroxide radical compounds selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, with other Rs if any representing hydrogen atoms, halogen atoms or hydroxy groups, and m is an integer from 20 to 5,000 while each n is independently an integer from 3 to 1,000.

In an uncharged state in water, the multiple molecules of this triblock copolymer form a molecular aggregate or so-called polymer micelle assembled with the CNR part as the core and the PEG part as the shell. Thus, it can be used for example as a drug delivery carrier because hydrophobic low-molecular-weight drugs can be sealed inside the core part if such drugs are included when forming these aggregates (the behaviors of ordinary polymer surfactants should be consulted as necessary). Moreover, a triblock copolymer containing an imino group in the linking group forms polycations in an acidic aqueous medium, and can be used to form a gel with a suitable anion. Such a gel composition is also a separate embodiment of the present invention, and can be used favorably for purposes of retention in an area of the body requiring elimination of active oxygen.

(Description of Invention)

As used in the invention of the application, a pendant group means a side chain having a particular functional group as commonly recognized in the technical field. Specifically, a pendant group is a group comprising a cyclic nitroxide radical residue covalently bound at the described right terminus to an o- or p-phenylene-$(C_{1-6}$ alkylene-NH$)_p(C_{1-6}$ alkylene$)_q$ or o- or p-phenylene-$(C_{1-6}$ alkylene-O$)_p$—$(C_{1-6}$ alkylene$)_q$ linking group (in which p is an integer from 1 to 3 and q is an integer from 0 to 1). More specifically, a pendant group in the present invention can be more clearly understood on the basis of reference to the side chain represented by -phenylene-$(C_{1-6}$ alkylene-NH$)_p$—$(C_{1-6}$ alkylene$)_q$-R or —$C_{1-6}$ alkylene-O—$(C_{1-6}$ alkylene$)_q$-R in General Formula (II) above. The main chain to which such a pendant group binds is not limited. In the present invention, a residue means a group obtained by removing one hydrogen atom from the corresponding compound, and in the case of a typical cyclic nitroxide radical the groups defined for R in General Formula (II) may be used as reference.

In a preferred embodiment of the pendant group, the cyclic nitroxide radical is bound to the polymer main chain via an o- or p-phenylene-$C_{1-6}$ alkylene-NH—$(C_{1-6}$ alkylene$)_q$ linking group (in which q is 0 or 1), and the cyclic nitroxide radical is itself selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxyazolidine-3-oxyl-2-yl, 2,4,4-trimethyl-1,3-thiazolidine-3-oxyl-2-yl and 2,4,4-trimethyl-imidazolidine-3-oxyl-2-yl.

In a triblock copolymer or polycation thereof in which the unbound terminal of phenylene is bound to the main chain, the "unbound terminal of phenylene" means the terminal at the opposite end from the binding position of the o- or p-phenylene $C_{1-6}$ alkylene. In the Description of this application, binding signifies covalent binding unless otherwise specified.

As discussed above, the polymer main chain is not limited as long as it is consistent with the object of the present invention, but preferably it is a main chain formed by radical polymerization of a polymerizable monomer having polymerizable unsaturated double bonds, such as a substituted ethylene having unsaturated double bonds for example. Specific examples of such main chains include those described in Patent Document 1 above.

A more preferred triblock copolymer is represented by General Formula (II).

[Chemical formula 2]

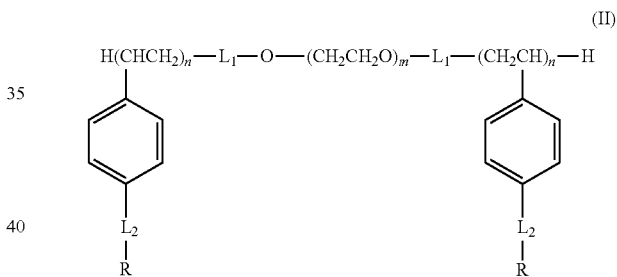

(II)

In the formula, each $L_1$ is independently selected from the group consisting of a single bond, —S—$(CH_2)_c$—, —S—$(CH_2)_cCO$—, —$(CH_2)_cS$— and —$CO(CH_2)_cS$—, in which c is an integer from 1 to 5 (the two groups listed after the single bond correspond to the left $L_1$ in a formula with the orientation shown above, while the next two correspond to the right $L_1$ in a formula with the orientation shown above); each $L_2$ is independently —$C_{1-6}$ alkylene-NH—$(C_{1-6}$ alkylene$)_q$- or —$C_{1-6}$ alkylene-O—$(C_{1-6}$ alkylene$)_q$-, in which q is 0 or 1; and at least 50%, or preferably at least 80%, or more preferably at least 90%, or most preferably about 100% of the total number n of Rs in the formula independently represent residues of cyclic nitroxide radical compounds selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxyazolidine-3-oxyl-2-yl, 2,4,4-trimethyl-1,3-thiazolidine-3-oxyl-2-yl and 2,4,4-trimethyl-imidazolidine-3-oxyl-2-yl, with other Rs if any representing hydrogen atoms, halogen atoms or hydroxy groups, and m in an integer from 20 to 5,000 or preferably 20 to 1,000 or more preferably 50 to 200, while each n is independently an integer from 3 to 1,000 or preferably 3 to 100 or more preferably 3 to 50.

The $C_{1-6}$ alkylene is not specifically limited, but examples include diyl groups of corresponding alkyls, such as methylene, 1,2-propanediyl, 1,3-propanediyl, 1,4-butanediyl and the like.

Preferred examples of R group cyclic nitroxide radicals include groups represented by the following formulae.

[Chemical formula 3]

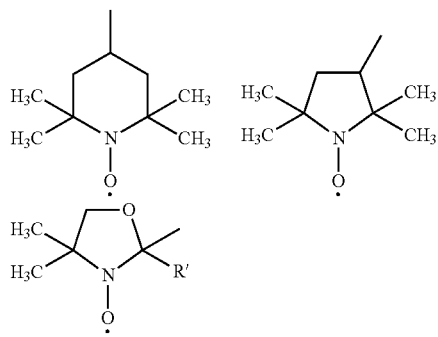

In the formulae, R' is a methyl group. The residue represented by the first formula above is abbreviated as TEMPO below.

Such a triblock copolymer can be manufactured conveniently by preparing a triblock copolymer precursor having the main chains or the main chains and some of the pendant groups, and then introducing nitroxide radical residues cyclically into the precursor. Another possible method is to prepare each of the blocks independently, and then bind them together so as to form the target triblock copolymer. In a typical manufacturing method, as shown in the examples below, this can be accomplished by either binding polymer segments capable of serving as CNR precursors to the termini of poly(ethylene glycol) which has been modified to make both termini reactive, or growing the segments from the termini, and then introducing a cyclic nitroxide radical bound via a linking group having at least one imino group or ether bond. Patent Document 1 describes a method of manufacturing a diblock copolymer comprising a polymer block corresponding to CNR and a polymer block corresponding to PEG, and once a triblock copolymer precursor of the present invention has been produced, the method described in Patent Document 1 can be consulted with respect to methods for completing the pendant groups in the present invention.

Of the triblock copolymers manufactured in this way, those having imino (—NH—) groups in the pendant groups are capable of forming salts with suitable inorganic or organic acids. These acids are not limited, but examples include inorganic acids such as hydrochloric acid, sulfuric acid, nitric acid and other mineral acids, and acetic acid, oxalic acid, methanesulfonic acid and other organic acids. Moreover, triblock copolymers having such imino groups are cationically chargeable in acidic aqueous media due to the presence of the imino groups, and can form polycations. Consequently, these polycations can form ion complexes with polyanions or compounds having one or more anionic groups. Examples of such compounds include enzymes such as esterases, while examples of polyanions include polyacrylic acid, polymethacrylic acid, polysulfonic acid, DNA, RNA, anionic proteins and the like.

Although the invention is not restricted by any theory, in this case a polyion complex consisting of equal amounts of polyanions and polycations becomes hydrophobic in an aqueous medium, forming the core of a hydrophilic-hydrophobic polymer micelle, while water-soluble PEG becomes a surface layer of loops that form a shell, thereby producing a so-called flower micelle as can be seen in the conceptual view of FIG. 1. Because this ion complex is highly sensitive to salt concentration and temperature, it breaks apart upon contact with bodily fluid at a temperature of 37° C. and an ion strength of 150 mM for example, producing a gel due to crosslinking between particles. It can be seen that because the aforementioned triblock copolymer has cyclic nitroxide radicals introduced into the polycation part, gelling is accompanied by surface exposure of the cyclic nitroxide radical part, which then functions to eliminate so-called bad active oxygen.

On the other hand, in a triblock copolymer having ether bonds (—O—) in the pendant groups, the part corresponding to the CNR segments exhibits hydrophobic properties in water, and thus forms a hydrophobic core by itself without formation of a polyion complex, while the water-soluble PEG becomes a surface layer of loops that form a shell, thereby producing a so-called flower micelle as can be seen in the conceptual view of FIG. 1. As discussed above, a hydrophobic low-molecular-weight drug can be sealed inside such a hydrophobic core. Therefore, while retaining the ability of the cyclic nitroxide radical part to eliminate bad active oxygen, the copolymer can be used as a delivery carrier for any poorly water-soluble drugs, which are not limited but include ifosfamide, cyclophosphamide, dacarbazine, temozolomide, nimustine, busulfan, melphalan, enocitabine, capecitabine, carmofur, gemcitabine, cytarabine, tegafur, tegafur-uracil, nelarabine, fluorouracil, fludarabine, pemetrexed, pentostatin, methotrexate, irinotecan, etoposide, sobuzoxane, docetaxel, nogitecan, paclitaxel, vinorelbine, vincristine, vindesine, vinblastine, actinomycin D, aclarubicin, idarubicin, epirubicin, daunorubicin, doxorubicin, pirarubicin, bleomycin, peplomycin, mitomycin C, mitoxantrone, oxaliplatin, carboplatin, cisplatin, nedaplatin and various other antineoplastic substances known in the technical field and Mucosta (rebamipide) and its analogs, vitamin E, beta-carotene, ubiquinone (coenzyme Q), bilirubin, catechin, resveratrol, tannins, ebselen, aminoeteroids, probucol, vitamin E analogs, eicosanoid metabolism inhibitors, carotenoids, retinoids, piperine and other poorly water soluble antibiotics, as well as vitamin E (ascorbic acid), glutathione, flavonoids, uric acid and other water-soluble antioxidants, superoxide dismutase, catalase, peroxidase, glutathione peroxidase, ceruloplasmin, metallothionein, thioredoxin and other proteinaceous antioxidants, and platinum colloid, fullerenes and other particulate antioxidants.

A composition containing a polyion complex or gel formed from the triblock copolymer described above may contain physiologically acceptable diluents such as sterile water, acidic aqueous solutions containing mineral acids, physiological saline, and solutions containing physiologically acceptable buffers and the like, or excipients such as sorbitol, dextrin, glucose, mannitol, amino acids (such as glycine, isoleucine, valine, methionine, glutamine, etc.) and the like.

This composition is capable of controlling inflammation either by a mechanism involving elimination of active oxygen that causes inflammation, or by another mechanism. Such inflammation is not limited, but may be associated with cerebral infarction, myocardial infarction, acute or chronic renal failure, Alzheimer's disease, Parkinson's disease, chromic occlusive pulmonary disease, diabetes, arteriosclerosis, hepatitis, digestive tract inflammation or the like. This composition may also be prepared so as to regulate fluidity in a specific area of the body, allowing it to be retained in that area. Areas of the body that are of interest to the inventors in this case are not limited, but include periodontal pockets, cancer lesions, arthritis and the like.

Thus, the present invention provides a composition for forming a gel, containing the aforementioned triblock copolymer or a polycation thereof and an aqueous medium (containing sterile water, an acid or buffer and sodium chloride and the like as necessary), which is preferably an aqueous medium with a pH of 3 to 10 or more preferably pH 4 to 8, or still more preferably with an acidic pH within these ranges. This composition can also be used as an active oxygen scavenger, and because of its property of localized retention in the body, it can be provided as a composition for purposes of retention in living bodies requiring elimination of active oxygen.

Moreover, inflammation can be prevented or treated by administering the composition (intravenously, arterially, subcutaneously, intramuscularly, or by another route) to a patient requiring control of inflammation

BRIEF DESCRIPTION OF THE DRAWINGS

FIG. 1 is a conceptual diagram showing the formation of a triblock copolymer flower micelle of the invention, and the formation of an injectable gel in a local area of the body in a suitable environment.

FIG. 2 shows the results of size exclusion chromatography (SEC) measurement and NMR spectrum measurement of a PCMS-b-PEG-b-PCMS triblock copolymer obtained in Manufacturing Example 1.

FIG. 3 shows SEC measurement and NMR spectrum measurement results for a PMNT-b-PEG-b-PMNT triblock copolymer obtained in Manufacturing Example 2.

FIG. 4 shows purification results for the same PMNT-b-PEG-b-PMNT triblock copolymer.

FIG. 5 shows the results of dynamic light scattering analysis of polyion complex micelles with different molar ratios obtained in Manufacturing Example 3, plotted against changes in the pH values of the polyion complex micelles.

FIG. 6 is a photograph in place of a drawing illustrating the gelling state of concentrated polyion complex micelles (r=1:1, 60 mg/ml).

FIG. 7 is a photograph in place of a drawing illustrating in vivo gelling of polyion complex micelles (r=1:1).

FIG. 8 is a graph showing body weight changes in mice after injection of a polyion complex.

FIG. 9 is an imaging photograph in place of a drawing illustrating local retention of a polyion complex gel (RIG).

FIG. 10 is a graph of (quantified) local retention of a polyion complex gel (RIG).

FIG. 11 is a graph of the protective effects of a polyion complex gel (RIG) in a carrageenan-induced inflammation model.

EXAMPLES

The invention is explained in more detail below with specific examples, but the intent is not to limit the present invention to these specific examples.

<Manufacturing Example 1> Synthesis of Polychloromethylstyrene-b-Polyethylene Glycol-b-Polychloromethylstyrene (PCMS-b-PEG-b-PCMS) Triblock Copolymer PCMS-b-PEG-b-PCMS was synthesized according to the following synthesis scheme 1:

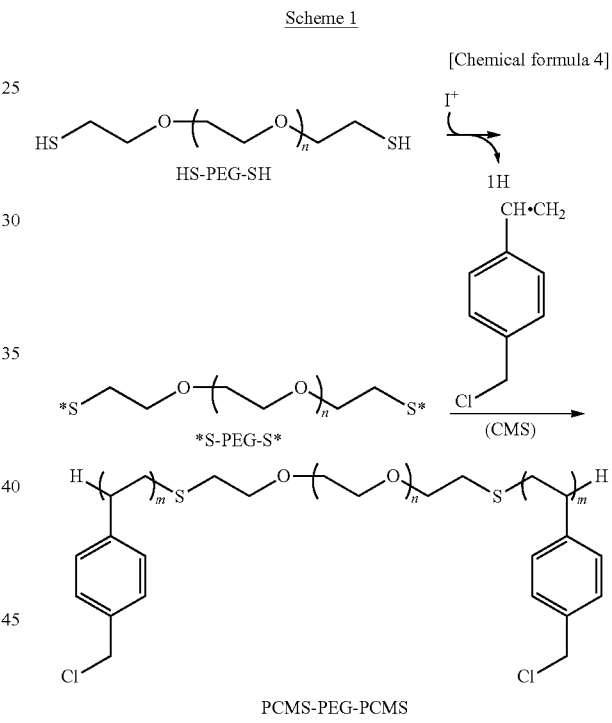

Poly(ethylene glycol) having thiol groups at both ends (HS-PEG-SH) (Mn: 10,000; 0.115 mmol, 1.15 g) was added to a reaction container. Next, the reaction container was vacuumized, and the operation of blowing in nitrogen gas was repeated three times to produce a nitrogen atmosphere in the reaction container. A 1.89 mg/mL azobisisobutyronitrile/toluene (0.115 mmol/10 ml) solution and chloromethylstyrene (8.63 mmol, 1.22 mL) were added to the reaction container, heated to 60° C., and agitated for 24 hours. The reaction mixture was washed three times with diethyl ether, which is a good solvent for poly(chloromethylstyrene) homopolymer, and then freeze-dried with benzene to obtain a white power. 1.45 mg was obtained for a yield of 91.6%. FIG. 2 shows the results of size exclusion chromatography (SEC) measurement and NMR spectrum analysis of the resulting PCMS-b-PEG-b-PCMS triblock copolymer.

<Manufacturing Example 2> Synthesis of Triblock Copolymer Having 2,2,6,6-tetramethylpiperidine-1-oxyl (TEMPO)

(1) Triblock copolymer of Formula (II) with —$CH_2$—NH— as L (PMNT-b-PEG-b-PMNT)

PCMS-b-PEG-b-PCMS (Mn: 13,800; 1.45 g, 0.105 mmol) was added to a reaction container. 4-amino-TEMPO (2.34 g, 13.69 mmol) was then dissolved in 12 mL of dimethylsulfoxide (DMSO), added to the reaction container, and agitated for 24 hours at room temperature. After completion of the reaction, the reaction solution was added to a dialysis membrane (Spectra/Por, molecular weight cutoff size 3,500, Spectrum Medical Industries Inc., Houston, Tex.), and dialysis was performed with 2 L of methanol. The methanol was exchanged 8 times every 2 hours, and the mixture was evaporated to and freeze-dried with benzene. The yield was 92.1%.

The results of $^1H$ NMR measurement confirmed 100% reaction of the chloromethyl groups and introduction of TEMPO (FIG. 3). The SEC results also showed that there were no side-reactions, and the chromatogram was similar to that of PCMS-b-PEG-b-PCMS. When this was sampled with SEC and the electron spin resonance (ESR) signals of each fraction were measured, the ESR signal for unreacted amino-TEMPO had disappeared, indicating that the unreacted amino-TEMPO had been completely removed by purification (FIG. 4).

(2) Triblock copolymer of Formula (II) with —$CH_2$—O— as $L_2$

The target triblock copolymer was manufactured by repeating operations similar to those described under (1) above except that 4-hydroxy-TEMPO was used instead of 4-amino-TEMPO, and dimethylformamide (DMF) dissolved in NaH was used for the reaction solution.

<Manufacturing Example 3> Design of Polyion Complex Micelle

PMNT-b-PEG-b-PMNT triblock polymer powder was dissolved in a 0.1 M HCl aqueous solution, the amino groups of the PMNT chains were completely protonated, and the polymer was collected by water-based freeze-drying. Next, the PMNT-b-PEG-b-PMNT triblock polymer and polyacrylic acid (PAA; Mn: 5,000) were each dissolved in $Na_2HPO_4$ buffer (0.1 M, pH 6.28), to prepare an anionic PAA aqueous solution and a cationic PMNT-b-PEG-b-PMNT aqueous solution with a concentration of 5 mg/ml. The PMNT-b-PEG-b-PMNT triblock polymer aqueous solution was dropped with agitation into the PAA aqueous solution, to prepare a polyion complex micelle. Four different polyion complex micelles were prepared with molar ratios r of PMNT-b-PEG-b-PMNT to PAA of 4:1, 2:1, 1:1 and 1:2 (molar ratio r=[moles of activated carboxyl groups of PAA]/[moles of activated amino groups of PMNT-b-PEG-b-PMNT]). The zeta potentials of the resulting polyion complex micelles were measured (see Table 1 below). Furthermore, polyion complex micelle solutions of each molar ratio were divided into 6 groups, and the pH values of each were varied from 4 to 8 with 0.01 M HCl/NaOH. When the average particle diameter of the resulting polyion complex micelles was measured by dynamic light scattering (DLS), they were found to be monomodal particles with an average diameter of 46 to 80 nm (see FIG. 5).

TABLE 1

Polyion complex micelle zeta potential measurement

| Molar Ratio r | Zeta potential (mV) |
|---|---|
| PAA | −4.33 |
| PMNT-PEG-PMNT | +3.76 |
| 4:1 | −3.73 |
| 2:1 | −2.24 |
| 1:1 | −0.119 |
| 1:2 | +1.43 |

<Manufacturing Example 4> Design of Injectable Gel

The polyion complex micelle solutions (5 mg/ml) prepared above with various molar ratios and pH values (molar ratio r=4:1, 2:1, 1:1; pH 4 to 8) were concentrated by centrifugal evaporation, the ion strength was adjusted to 150 mM, and gelling was investigated by the test tube inversion method in a water bath at 37° C. An investigation of optimal pH and concentration conditions relative to the molar ratio of polyion complex micelles irreversibly gelled under conditions of ion strength 150 mM, temperature 37° C. revealed that gelling occurred under conditions of 40 mg/ml, pH 5 when the molar ratio r was 4:1, 50 mg/ml, pH 4 to 5 when the molar ratio r was 2:1, and 60 mg/ml, pH 6 to 6 when the molar ratio r was 1:1 (see Table 2 below and FIG. 6).

TABLE 2

Gelling conditions for polyion complex micelles at 37° C., ion strength 150 mM

| Molar ratio r | 4:1 | 2:1 | 1:1 |
|---|---|---|---|
| Concentration (mg/ml) | 40 | 50 | 60 |
| pH 4 | Gel (25° C.) | Injectable gel | Liquid |
| pH 5 | Injectable gel | Injectable gel | Injectable gel |
| pH 6 | Gel (25° C.) | Liquid | Injectable gel |
| pH 7 | Precipitate (25° C.) | — | Gel (25° C.) |
| pH 8 | Precipitate (25° C.) | Precipitate (25° C.) | Precipitate (25° C.) |

<Test 1> In Vivo Gel Formation

Polyion complexes (5 mg/ml, 9 ml) with a 1:1 molar ratio r of PMNT-b-PEG-b-PMNT to PAA were prepared in accordance with Manufacturing Example 3 and divided into two groups, the pH was adjusted to 5 and 6 with a 0.1 M HCl aqueous solution, and the solutions were concentrated to 50 mg/ml by centrifugal evaporation. When 100 μl of each of the concentrated micelle solutions with the respective pH values was injected subcutaneously to the left thighs of mice, gel formation was confirmed inside the mouse bodies, and tissue adhesiveness was also observed (Table 3, FIG. 7). However, gelling was not confirmed when the molar ratio was 2:1 (pH 4, 5, 6).

TABLE 3

In vivo gelling results for polyion complex micelles

| Molar ratio r | 2:1 | | | 1:1 | |
|---|---|---|---|---|---|
| Concentration (mg/ml) | 50 | | | 60 | |
| pH | 4 | 5 | 6 | 5 | 6 |
| In vivo gelling | Δ | Δ | Δ | ◯ | ◯ |

<Test 2> Injectable Gel Toxicity Test

To evaluate the in vivo toxicity of the gel, a 60 mg/ml polyion complex was prepared with a molar ratio r of 1:1 and a pH of 6, 100 µl and 50 µl were injected subcutaneously into the left thighs and right hind paws, respectively, of 10 mice, and changes in the body weight of the mice were recorded over the course of 4 weeks. The results showed that the body weights of the mice rose gradually, and the survival rate was 100% (see FIG. 8). These results show that the toxicity of an injectable gel developed by the present invention is extremely low.

<Test 3> Local Retention of Injectable Gel (Imaging by L-Band Electron Spin Resonance)

Three mice were used in each group. 70 µl of a solution of the nitroxide radical-containing polyion complex micelles used in Test 1 (PMNT-b-PEG-b-PMNT to PAA molar ratio r=1:1 (RIG). pH 6, 60 mg/ml) was injected subcutaneously into the left hind paws of three mice. For the control groups, 70 µl each of a low-molecular-weight nitroxide radical compound (4-aminoTEMPO; 5.45 mg/ml), a micelle solution of a nitroxide radical-containing polymer (polymer micelles formed by dialysis from a PEG-b-PMNT amphiphilic block copolymer) ($RNP^N$; 60 mg/ml, and a solution mixed with low-molecular-weight 4-aminoTEMPO physically encapsulated in polyion complex micelles without nitroxide radicals (formed by mixing 4-aminoTEMPO with TEMPO-free flower micelles (nRIG) formed using a polymer with amino ethanol introduced instead of TEMPO, and gelling as is to encapsulate the 4-aminoTEMPO inside the gel) (nRIG+4-aminoTEMPO; molar ratio r=1:1, pH 6, 60 mg/ml) was injected into the right hind paws of three mice. Local retention of nitroxide radicals in the mouse paws was imaged by L-band electron spin resonance (ESR) using mice immediately after administration. In the case of the low-molecular-weight 4-aminoTEMPO solution, the ESR signal disappeared from the mouse paws within 30 minutes after administration. Although retention was slightly improved with the $RNP^N$ solution containing micelles of 4-aminoTEMPO, the signal disappeared after an hour. Similarly, retention was only observed for up to an hour due to dispersion with the nRIG-containing gel mixed with 4-aminoTEMPO. By contrast, when RIG was gelled in the soles of mice injected with the polyion complex micelle solution of the present invention, a strong ESR signal was detected through a 5-hour period during measurement. Thus, a gel formed from the polyion complex micelles of the present invention is confirmed to have excellent local retention. Photographs are included in place of drawings illustrating the imaging (see FIG. 9).

Thus, it has been confirmed that evaluation methods using non-invasive imaging are ordinarily suited to evaluating residual drug quantities and for evaluating the degree of oxidative stress.

<Test 4> Local Retention of Injectable Gel (Quantified by X-Band Electron Spin Resonance)

Three mice (n=3) were used in each of the four groups (4-aminoTEMPO, $RNP^N$, RIG, nRIG+4-aminoTEMPO). 50 µl each of the low-molecular-weight nitroxide radical compound 4-aminoTEMPO (5.45 mg/ml), a solution of nitroxide radical-containing polymer micelles ($RNP^N$; 60 mg/ml), a solution of nitroxide radical-containing polyion complex micelles (RIG: molar ratio r=1:1, pH 6, 60 mg/ml), and a solution of low-molecular-weight 4-aminoTEMPO physically mixed with polyion complex micelles without nitroxide radicals (nRIG+4-aminoTEMPO: molar ratio r=1:1, pH 6, 60 mg/ml) was injected subcutaneously into the right hind paws of the mice. The mice were dissected at different intervals (0 h, 1 h, 3 h, 12 h, 24 h, 72 h) after administration, and a homogenized solution of the tissue of the collected right hind paws with potassium ferricyanide (200 mN) added as an oxidizing agent was subjected to X-band electron spin resonance to quantify local retention at each time interval. The result is shown in FIG. 10.

With the low-molecular-weight compound (4-aminoTEMPO) and the mixed nRIG gel with 4-aminoTEMPO (nRIG+4-aminoTEMPO), the gel was eliminated by dispersion from the administration site within 1 hour. In the case of the polymer micelles consisting of a TEMPO-containing diblock polymer (RNP), the gel was eliminated from the administration site within 12 hours, while with RIG 40% of the gel remained even after 72 hours. These results confirm that RIG exhibits excellent local retention properties.

<Test 5> Protective Effect of Injectable Gel in Carrageenan-Induced Arthritis Model Five mice (n=5) were used in each of 9 groups (Control, RIG, nRIG, Saline@Carr, RIG@Carr, nRIG@Carr, 4-amino-TEMPO@Carr, $RNP^N$@Carr, nRIG+4-aminoTEMPO@Carr).

The tested groups are defined as follows.

Control: discussed below

RIG: TEMPO-containing gel formed in vivo after administration of TEMPO-containing flower micelles nRIG: Gel without TEMPO formed in vivo after administration of flower micelles containing no TEMPO Saline@Carr: Carrageenan administered 18 hours after administration of physiological saline RIG@Carr: Carrageenan administered 18 hours after administration of TEMPO-containing flower micelles nRIG@Carr: Carrageenan administered 18 hours after administration of flower micelles containing no TEMPO 4-amino-TEMPO@Carr: Carrageenan administered 18 hours after administration of 4-amino-TEMPO $RNP^N$@Carr: Carrageenan administered 18 hours after administration of TEMPO-containing polymer micelles nRIG+4-amino-TEMPO@Carr: Carrageenan administered 18 hours after administration of TEMPO-free flower micelles encapsulating 4-amino-TEMPO After the mice had fasted for 6 hours, the pain hypersensitivity of the hind paws of normal mice was evaluated in a heat stimulus test (51° C.) using a hot plate. The time taken until the mice began to lick, pull or shiver their hind paws on the hot plate was given as the Paw Withdrawal Latency (PWL). 50 µl each of nitroxide radical-containing polyion complex micelles for forming an RIG gel (RIG; molar ratio r=1:1, pH 6, 60 mg/ml), nitroxide radical-free polyion complex micelles for forming an nRIG gel (nRIG; molar ratio r=1:1, pH 6, 60 mg/ml), saline, a low-molecular-weight nitroxide radical compound solution (4-aminoTEMPO; 5.45 mg/ml), a nitroxide radical-containing polymer micelle solution ($RNP^N$; 60 mg/ml), and a solution of low-molecular-weight 4-aminoTEMPO physically mixed with nitroxide radical-free polyion complex micelles (n-RIG+4-aminoTEMPO; molar ratio r=1:1, pH 6, 60 mg/ml) was then injected subcutaneously into the right hind paws of mice. 18 hours later, 50 µl of 5% carrageenan buffer was injected subcutaneously into the right hind paws of the mice in the Saline@Carr, RIG@Carr, nRIG@Carr, 4-amino-TEMPO@Carr, $RNP^N$@Carr, and nRIG+4-aminoTEMPO@Carr groups (n=5). Nothing was administered to the Control group (n=5). 6 hours after carrageenan administration, the heat stimulus test was performed again using the hot plate. The time difference in Paw Withdrawal Latency (PWL) after subtraction of the PWL time after occurrence of inflammation from the PWL time before occurrence of inflammation is shown on the vertical axis of the to graph. The greater the time difference, the greater the degree of inflammation. The collected tissue of the mouse right hind paws was then homogenized, and the amount of inflammatory cytokines (TNF-α and IL-1β) and myeloperoxidase (MPO) activity as a marker of neutrophil infiltration were measured with an ELISA kit in the supernatant collected by centrifugation. The results are shown in FIG. 11.

As shown in the figure, increased MPO activity was confirmed in the blood and locally in the paws of the group receiving only nRIG without nitroxide radicals. This activity was significantly constrained in the RIG group. These results suggest that RIG itself does not cause inflammation. In the Saline@Carr, nRIG@Carr, 4-amino-TEMPO@Carr, RNP$^N$@Carr and nRIG+4-aminoTEMPO@Carr groups, MPO activity caused by carrageenan was not significantly suppressed, but in the RIG@Carr group MPO activity was significantly suppressed.

Similarly, the RIG gel significantly suppressed the occurrence of the inflammatory cytokines TNF-α and IL-1β, effectively preventing carrageenan-induced pain hypersensitivity. These results suggest that the RIG gel effectively eliminates active oxygen produced by neutrophils and macrophages.

INDUSTRIAL APPLICABILITY

The triblock copolymer of the present invention can be used not only as an active component of a composition for forming a gel when injected into a living body, but also as an in vivo active oxygen scavenger because it carries cyclic nitroxide radicals in the polymer. Thus, the present invention can be used in medical manufacturing and the like.

The invention claimed is:

1. A composition comprising:
a polyion complex comprising a polyanion selected from the group consisting of poly(acrylic acid), poly(methacrylic acid), poly(sulfonic acid), DNA, RNA and anionic proteins, and a triblock copolymer or salt thereof of following formula:

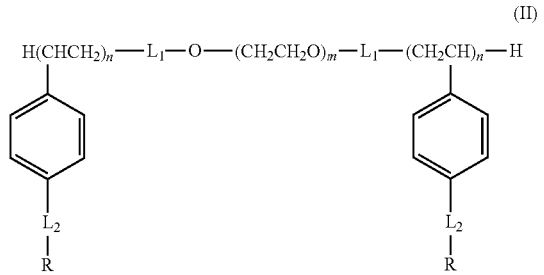

(II)

wherein each $L_1$ is independently selected from the group consisting of a single bond, —S—$(CH_2)_c$—, —S—$(CH_2)_c CO$—, —$(CH_2)_c S$— and —$CO(CH_2)_c S$—, in which c is an integer from 1 to 5; each $L_2$ is independently —$C_{1-6}$ alkylene-NH—$(C_{1-6}$ alkylene$)_q$-, in which q is the integer 0 or 1; and at least 50% of the total number n of R in the formula independently represent residues of cyclic nitroxide radical compounds selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxyazolidine-3-oxyl-2-yl, 2,4,4-trimethyl-1,3-thiazolidine-3-oxyl-2-yl and 2,4,4-trimethyl-imidozolidine-3-oxyl-2-yl, with other R if any representing hydrogen atoms, halogen atoms or hydroxy groups, and m is an integer from 20 to 5,000 while each n is independently an integer from 3 to 1,000,
wherein the polyion complex is in the form of a polyion complex micelle in $Na_2HPO_4$ buffer (0.1M) at pH 6.28,
wherein said composition forms a gel when injected into a living body and said gel is retained in a specific area of the body selected from the group consisting of a periodontal pocket, a cancer lesion and a site affected by arthritis; and wherein the composition further provides at least one property selected from the group consisting of suppressing inflammation, scavenging active oxygen, and regulating fluidity.

2. A method for suppressing inflammation, comprising administering the composition according to claim 1 to a patient requiring elimination of active oxygen.

3. The composition according to claim 1, further comprising a physiologically acceptable diluent or excipient.

4. The composition according to claim 1, wherein the polyanion is selected from the group consisting of poly(acrylic acid), poly(methacrylic acid), and poly(sulfonic acid).

5. The composition according to claim 1, wherein in the triblock copolymer m is an integer from 20 to 1,000.

6. The composition according to claim 1, wherein in the triblock copolymer m is an integer from 50 to 200.

7. The composition according to claim 1, wherein in the triblock copolymer each n is independently an integer from 3 to 100.

8. The composition according to claim 1, wherein in the triblock copolymer each n is independently an integer from 3 to 50.

9. The composition according to claim 1, wherein in the triblock copolymer R is selected from the groups represented by the following formulae:

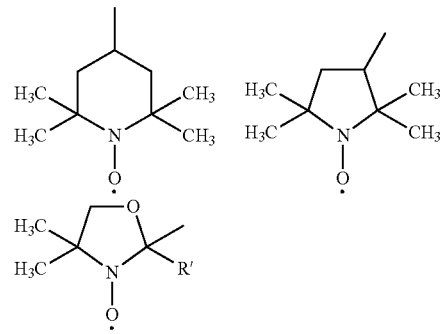

in which R' is a methyl group, and groups represented by these formulae constitute at least 80% of the total number n of R.

* * * * *